(12) United States Patent
Moore, III et al.

(10) Patent No.: US 10,286,594 B2
(45) Date of Patent: May 14, 2019

(54) BATCH THERMOFORMER FOR DENTAL APPLIANCES

(71) Applicants: Marbert G. Moore, III, Liberty Hill, TX (US); Edgar E. C. Stone, Round Rock, TX (US); Francisco Rodriguez, Jarrel, TX (US)

(72) Inventors: Marbert G. Moore, III, Liberty Hill, TX (US); Edgar E. C. Stone, Round Rock, TX (US); Francisco Rodriguez, Jarrel, TX (US)

(73) Assignee: ClearCorrect Operating, LLC, Round Rock, TX (US)

(*) Notice: Subject to any disclaimer, the term of this patent is extended or adjusted under 35 U.S.C. 154(b) by 412 days.

(21) Appl. No.: 14/952,243

(22) Filed: Nov. 25, 2015

(65) Prior Publication Data

US 2017/0144360 A1 May 25, 2017

(51) Int. Cl.
*A61C 13/08* (2006.01)
*B29C 51/18* (2006.01)
(Continued)

(52) U.S. Cl.
CPC ............ *B29C 51/18* (2013.01); *A61C 7/08* (2013.01); *B29C 51/10* (2013.01); *B29C 51/425* (2013.01);
(Continued)

(58) Field of Classification Search
CPC ....... B29C 51/425; B29C 51/18; B29C 51/46; B29C 51/10; A61C 7/08
See application file for complete search history.

(56) References Cited

U.S. PATENT DOCUMENTS 3,600,752 A 8/1971 Kopp
3,632,252 A 1/1972 Amberg et al.
(Continued)

OTHER PUBLICATIONS

US 3,682,517 A, 08/1972, Greenberg et al. (withdrawn)
(Continued)

*Primary Examiner* — Galen H Hauth
(74) *Attorney, Agent, or Firm* — Intella IP; James W. Pravel

(57) ABSTRACT

The present invention is directed to a system for thermoforming a batch of dental appliances simultaneously. An embodiment of the invention includes a vacuum plate having an upper surface and a plurality of cups for receiving dental models. A polymer sheet extends over the upper surface of the vacuum plate and over the cups. A heater cap that is movable in proximity to the cups is provided to heat the polymer sheet to be formed onto the dental models. The vacuum plate is configured to create a vacuum seal between an upper edge of the cups and the polymer sheet. A vacuum source is provided to apply a vacuum to the cups below the polymer sheet wherein the pressure contained in said cups is lower than atmospheric pressure whereby at least a portion of the polymer sheet is drawn into each of the cups and drawn over the dental models to form an aligner over each of the dental models. The invention includes the process of drawing a vacuum in a series of steps, or phases, to the cups below the polymer sheet to form the polymer effectively around the dental model.

16 Claims, 15 Drawing Sheets

(51) Int. Cl.
*A61C 7/08* (2006.01)
*B29C 51/10* (2006.01)
*B29C 51/42* (2006.01)
*B29C 51/46* (2006.01)
*B29K 75/00* (2006.01)
*B29L 31/00* (2006.01)

(52) U.S. Cl.
CPC .......... *B29C 51/46* (2013.01); *B29K 2075/00* (2013.01); *B29L 2031/753* (2013.01)

(56) References Cited

U.S. PATENT DOCUMENTS

| | | | |
|---|---|---|---|
| 3,682,580 A | | 8/1972 | Greenberg et al. |
| 3,712,780 A | * | 1/1973 | Jope .................. B29C 33/305 |
| | | | 249/120 |
| 3,770,546 A | * | 11/1973 | Childress ............... B29C 51/12 |
| | | | 156/245 |
| 3,891,736 A | * | 6/1975 | Voaden .................. B29C 51/10 |
| | | | 264/553 |
| 3,960,471 A | * | 6/1976 | Medendorp ............ B29C 51/34 |
| | | | 264/553 |
| 4,567,932 A | | 2/1986 | Hollenbach |
| 4,609,349 A | | 9/1986 | Cain |
| 4,692,111 A | * | 9/1987 | Wagner ................. B29C 33/46 |
| | | | 425/388 |
| 4,909,723 A | | 3/1990 | Slat et al. |
| 5,217,563 A | | 6/1993 | Neibling et al. |
| 5,242,304 A | | 9/1993 | Truax et al. |
| 5,468,135 A | | 11/1995 | Thomas |
| 5,667,386 A | | 9/1997 | Black et al. |
| 5,693,268 A | | 12/1997 | Widman et al. |
| 5,829,980 A | * | 11/1998 | Sheridan .................. A61C 7/00 |
| | | | 433/213 |
| 5,975,893 A | | 11/1999 | Chishti et al. |
| 6,077,075 A | | 6/2000 | Bedard et al. |
| D428,901 S | * | 8/2000 | Taylor, Jr. .................... D15/135 |
| 6,379,606 B1 | | 4/2002 | Chun et al. |
| 6,403,014 B1 | | 6/2002 | Hendry et al. |
| 6,524,101 B1 | | 2/2003 | Phan et al. |
| 6,705,853 B1 | | 3/2004 | Nehring |
| 6,737,619 B2 | | 5/2004 | Seghatol et al. |
| 6,976,627 B1 | | 12/2005 | Culp et al. |
| 7,018,208 B2 | | 3/2006 | Buresten |
| 7,037,111 B2 | | 5/2006 | Miller |
| 7,045,086 B2 | | 5/2006 | Fitzell, Jr. |
| 7,063,811 B2 | | 6/2006 | Brozenick et al. |
| 7,201,575 B2 | | 4/2007 | Adell et al. |
| 7,261,533 B2 | | 8/2007 | Wrosz et al. |
| 7,306,152 B2 | | 12/2007 | Culp et al. |
| 7,572,121 B2 | | 8/2009 | Wrosz et al. |
| 7,611,058 B2 | | 11/2009 | Culp et al. |
| 7,648,360 B2 | | 1/2010 | Kuo |
| 7,758,346 B1 | | 7/2010 | Letcher |
| 8,226,393 B2 | | 7/2012 | Patel |
| 8,261,748 B1 | | 9/2012 | Goldberg |
| 8,282,382 B2 | | 10/2012 | Mazzarolo |
| 8,393,371 B2 | | 3/2013 | Bryant et al. |
| 8,439,671 B2 | | 5/2013 | Cinader, Jr. |
| 8,501,054 B2 | | 8/2013 | Lee et al. |
| 8,607,798 B2 | | 12/2013 | Turkbas et al. |
| 8,634,948 B2 | | 1/2014 | Boronvinskih et al. |
| 8,690,568 B2 | | 4/2014 | Chapoulaud et al. |
| 8,758,009 B2 | | 6/2014 | Chen et al. |
| 8,899,977 B2 | | 12/2014 | Cao et al. |
| 8,961,173 B2 | | 2/2015 | Miller |
| 8,992,215 B2 | | 3/2015 | Chapoulaud et al. |
| 8,995,732 B2 | | 3/2015 | Kaza et al. |
| 9,017,072 B2 | | 4/2015 | Kitching et al. |
| 9,022,781 B2 | | 5/2015 | Kuo et al. |
| 2002/0110780 A1 | | 8/2002 | Zegarelli |
| 2003/0075840 A1 | * | 4/2003 | Hahn .................. B29C 43/3607 |
| | | | 264/571 |
| 2004/0118546 A1 | | 6/2004 | Bakken et al. |
| 2006/0068169 A1 | | 3/2006 | Hanada et al. |
| 2006/0102725 A1 | | 5/2006 | Culp et al. |
| 2006/0240374 A1 | * | 10/2006 | Wen .......................... A61C 7/08 |
| | | | 433/24 |
| 2007/0031790 A1 | | 2/2007 | Raby et al. |
| 2010/0181691 A1 | | 7/2010 | Yoshida |
| 2012/0040327 A1 | | 2/2012 | Kohl et al. |
| 2014/0315513 A1 | | 10/2014 | Long |
| 2015/0044627 A1 | | 2/2015 | German |

OTHER PUBLICATIONS

Great Lakes Orthodontics, LTD, MiniSTAR S with Scan Technology Operation Manual, Date of document creation Feb. 1, 2012, Date of retrieval on Internet Sep. 21, 2015.
Great Lakes Orthodontics, LTD, Biostar Scan/Biostar V Operation Manual, Date of document creation Oct. 7, 2010, Date of retrieval on Internet Oct. 27, 2015.
The Dental Warrior—A Blog for Dentists, Great Lakes Ortho Ministar—Product Review, Date of retrieval on Internet Sep. 21, 2015.
Erkodent Erich Kopp GmbH, Erkoform—3d Instructions, Date of document creation Jan. 13, 2009, Date of retrieval on Internet Sep. 14, 2015.
Zendura, Material Flyer, Date of document creation Apr. 24, 2014, Date of retrieval on Internet Sep. 14, 2015.
Zendura, Common Questions, Date of retrieval on Internet Sep. 14, 2015.
Zendura, The ZenduraDental Blog, Date of retrieval on Internet Sep. 14, 2015.
Zendura, Zendura—ClearCorrect Provider Price, Date of retrieval on Internet Sep. 15, 2015.

* cited by examiner

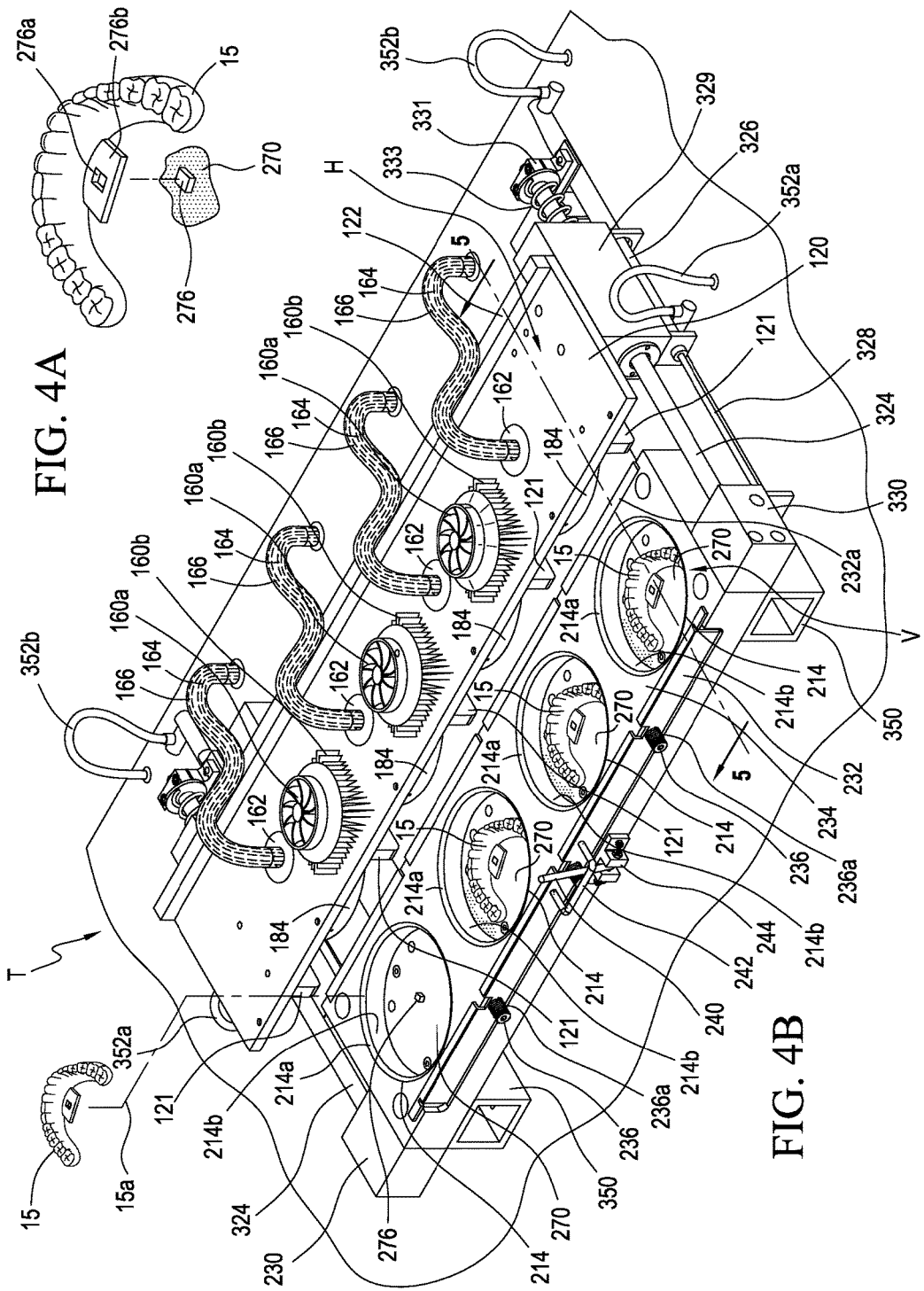

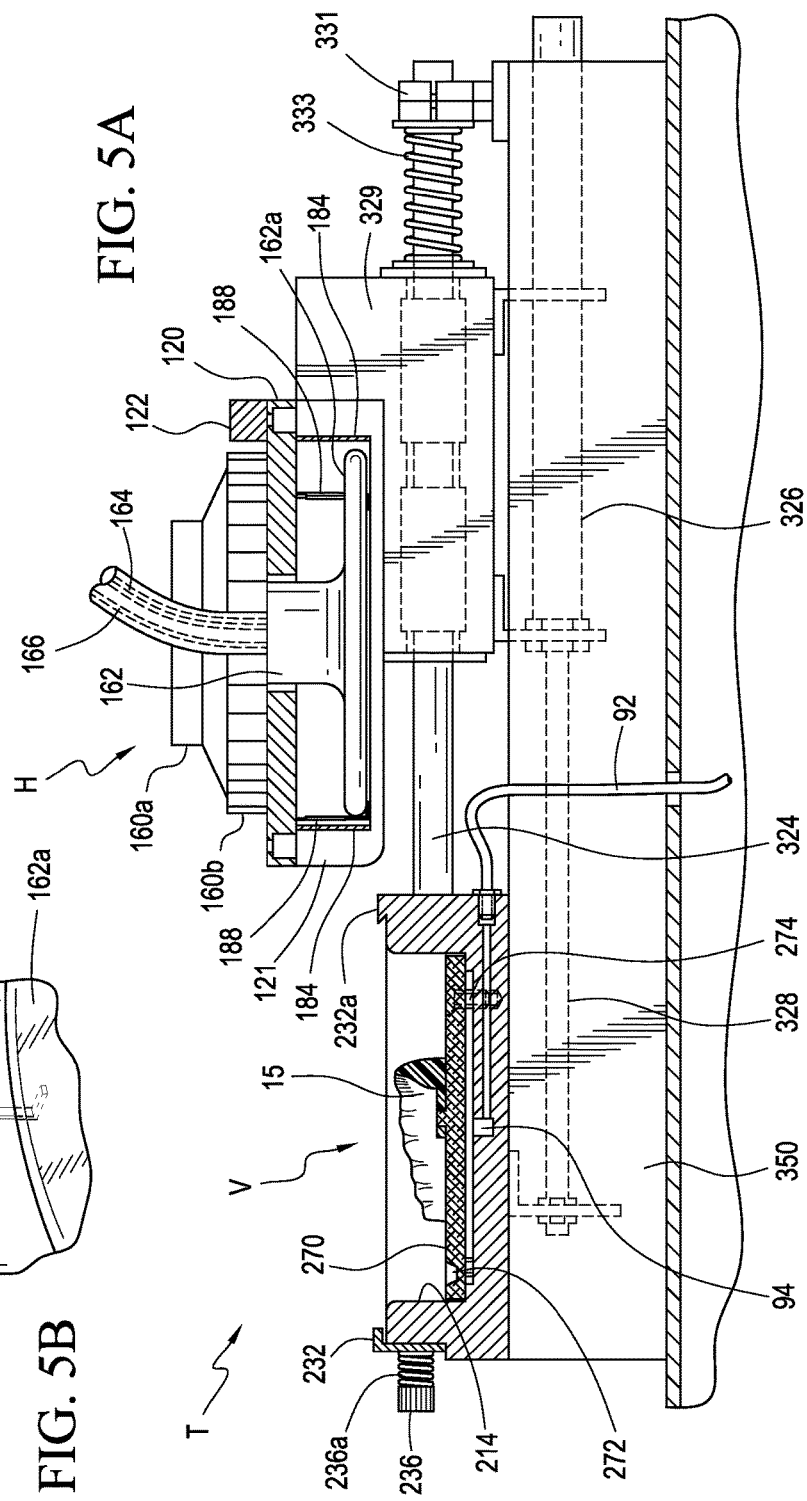
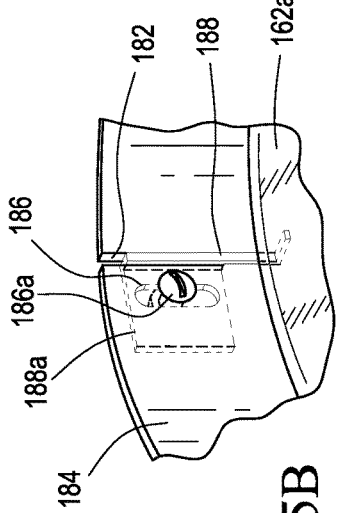
FIG. 5A
FIG. 5B

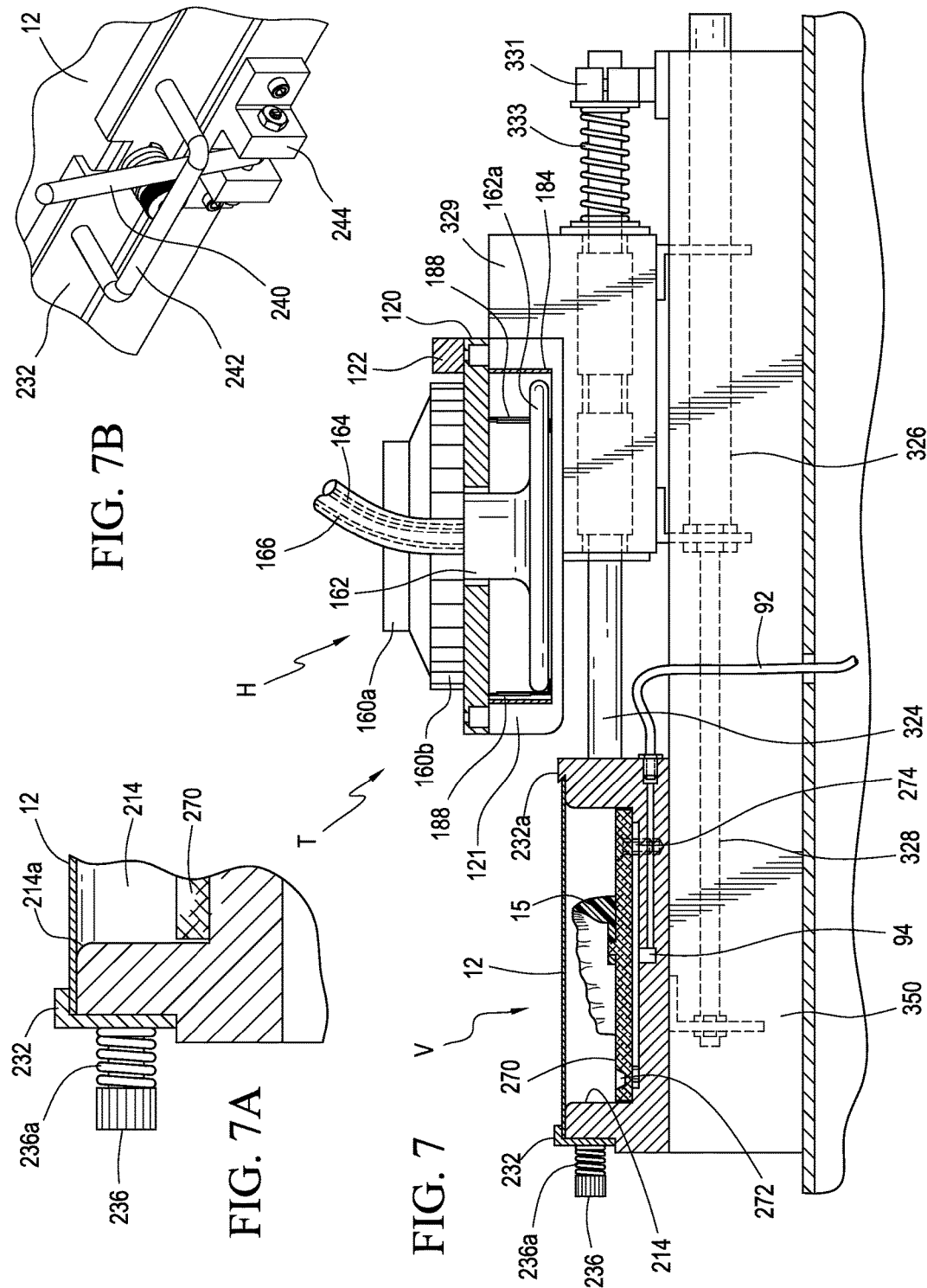

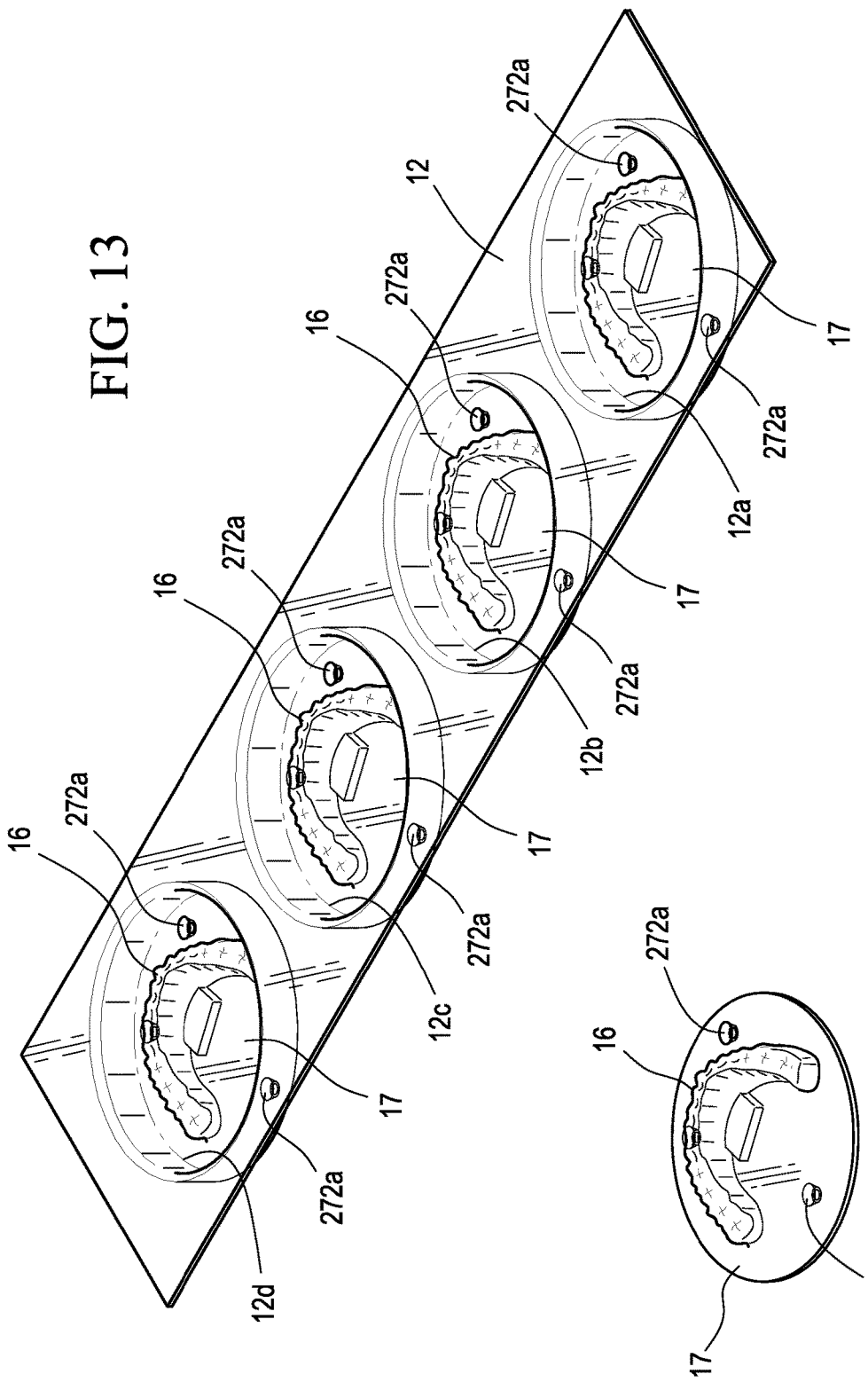

BATCH THERMOFORMER FOR DENTAL APPLIANCES

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The field of the invention is dental appliance manufacturing.

2. Description of the Related Art

Orthodontic aligners are appliances intended to make a series of discrete tooth position corrections aimed at aligning the teeth correctly. Aligners are equivalent to having bracket/wire braces for orthodontic treatment but they have many advantages. For example, aligners are invisible, comfortable and removable for cleaning and they allow a patient to eat anything they want. The manufacture of aligners begins with making stone models from dental impressions that come from orthodontists. The stone models of the dental impressions provide a positive model of the teeth, also known as the dental arch.

The stone models are scanned electronically to produce three dimensional computer aided design (CAD) representations to be imported by custom software. The custom software allows the operator to move individual teeth in specific and discrete movements to achieve the final dental arch of aligned teeth. The typical tooth movement is 0.1 mm per week.

Each aligner is meant to be worn for three weeks, then the patient moves on to wear the next aligner. A patient will typically wear aligners for somewhere between 18 to 36 weeks. For example, a treatment that takes 18 weeks is 6 pairs of aligners, including upper and lower dental arches.

The software allows the operator to create a stepwise sequence of teeth positions from start to finish via 6 stages, for example for an 18 week treatment plan. In the 18 week example, the software will create 6 pairs of models of dental arches. The resulting adjusted and predictive models of the dental arches are then printed as 3D models.

The 3D models are washed and then the models are allowed to dry. Once dried, a polymer is thermoformed over the top of the 3D model.

The thermoformed part is then laser marked with part identification. The laser marked, thermoformed part is then cut by one of several methods so that the aligner that goes to the customer can be separated from the carrier frame of plastic.

The aligner is then polished in a part tumbling process to remove burrs and sharp edges. The aligners are inspected and then sealed in bags to be shipped to the customer's orthodontist.

The aligners are currently thermoformed individually. For example, the Biostar® thermoformer, by Great Lakes Orthodontics, Ltd., uses positive pressure to thermoform a single aligner. The Biostar® thermoformer also does not allow full and variable control of the heater that is used to heat the polymer during the thermoforming process.

An aligner thermoformer that is capable of producing a series of aligners is shown in U.S. Pat. No. 7,261,533 ("the '533 patent"). The '533 patent is highly complex and does not allow for the production of a batch of aligners simultaneously. It also has one production speed and must be operated in a continuous mode, which does not allow the operator to make just a single aligner. While the temperature set point can be adjusted on the '533 patent, the temperature set point will apply to all aligners as they are produced in series. The '533 patent employs positive pressure to thermoform each aligner while vacuum is used to prevent bubbles from forming during the thermoforming process.

What is needed is a thermoformer for manufacturing aligners that produces a batch of aligners with the ability to control the temperature set point for each aligner forming location. The number of aligners to be produced could be increased by increasing the number of thermoforming stations.

The new thermoformer should also only use vacuum to evacuate the gas out of the region between the softened polymer and the dental model to more exactly conform the aligner to the dental model. The more accurate adaptation of aligners to the dental models will result in better performance of the aligners for patients and customers.

The new thermoformer should make parts faster and it should cost less than existing technology. It should also allow more control of the thermoforming process.

BRIEF SUMMARY OF THE INVENTION

The present invention is directed to a system for thermoforming a batch of dental appliances simultaneously. An embodiment of the invention includes a vacuum plate having an upper surface and a plurality of cups for receiving dental models. A polymer sheet extends over the upper surface of the vacuum plate and over the cups. A heater cap that is movable in proximity to the cups is provided to heat the polymer sheet to be formed onto the dental models. The vacuum plate is configured to create a vacuum seal between an upper edge of the cups and the polymer sheet. A vacuum source is provided to apply a vacuum to the cups below the polymer sheet wherein the pressure contained in said cups is lower than atmospheric pressure whereby at least a portion of the polymer sheet is drawn into each of the cups and drawn over the dental models to form an aligner over each of the dental models.

The vacuum seal between the upper edge of the cups and the polymer sheet is created from a rounded surface at an upper edge of the cups where the upper edge of the cups intersects the upper surface of the vacuum plate.

The heater cap includes a plurality of heating elements with each heating element aligned to provide heat in proximity to each of the cups. Each of the heating elements includes a thermocouple in communication with a controller to individually monitor and adjust the temperature of the heating elements whereby the temperature of each of the cups can be controlled independently. A plurality of cooling fans is typically provided on the heater cap to regulate the temperature of the heater cap.

An adapter plate having a plurality of orifices is positioned in each of the cups whereby vacuum pressure applied by the vacuum source through the orifices in the adapter plate to effect uniform molding of the polymer sheet about the dental model to form the aligner. The adapter plate comprises a sintered metallic material, such as sintered bronze. The adapter plate includes an alignment feature to orient the dental model in a desired location to enable later processing of the aligner. The alignment feature comprises a peg, pegs or other locating features, integral with the adapter plate, onto which the dental model is secured.

The heater cap includes a plurality of bosses adapted to insure the polymer sheet is presented to the upper surface of the vacuum plate to prevent air from escaping from between the polymer sheet and the cup when the heater cap is in proximity to the vacuum plate and when the vacuum source draws a vacuum in the cup.

At least one cylinder is provided to extend and retract the heater cap to position the heater cap in proximity to the vacuum plate. A spring is positioned behind the at least one cylinder to dampen the heater cap when the heater cap is opened. Pneumatic or fluid pressure is applied to at least one cylinder to extend and retract the heater cap.

A fixed stop is provided on the upper surface of the vacuum plate positioned to engage a back edge of the polymer sheet and an adjustable stop is provided on the upper surface of the vacuum plate positioned to engage a front edge of the polymer sheet, wherein the front edge is substantially parallel to the back edge of the polymer sheet whereby the polymer sheet can be positioned as desired relative to the cups.

The vacuum source draws a vacuum to approximately 1.0 psia.

The present invention is also directed to a method of thermoforming a batch of dental appliances simultaneously comprising the steps of:

a. Providing a vacuum plate with an upper surface and a plurality of cups for receiving dental models;
b. Extending a polymer sheet over the upper surface of the vacuum plate and over the cups;
c. Positioning a heater cap that is movable in proximity to the cups to heat the polymer sheet onto the dental models;
d. Configuring a vacuum plate to create a vacuum seal between an upper edge of the cups and the polymer sheet; and
e. Applying a vacuum to the cups below the polymer sheet wherein the pressure contained in the cups is lower than atmospheric pressure whereby at least a portion of the polymer sheet is drawn into each of the cups and drawn over the dental models to form an aligner over each of the dental models.

The method of thermoforming a batch of dental appliances simultaneously can also comprise the additional step of including a plurality of heating elements with each heating element aligned to provide heat in proximity to each of the cups.

The method of thermoforming a batch of dental appliances simultaneously can also comprise the additional step of applying vacuum in a series of at least one additional phase to the cups below the polymer sheet to form the polymer effectively around the dental model. Multiple vacuum phases may also be applied.

BRIEF DESCRIPTION OF THE DRAWINGS

FIG. 4A shows a perspective assembly view of an embodiment of an inventive dental model and the inventive peg from an inventive adapter plate.
FIG. 4B shows a perspective view of an embodiment of the inventive thermoformer with three dental models, each in a cup, and one dental model out of a cup but in position to be received in a cup.
FIG. 5A shows a side section view taken along line 5-5 of FIG. 4B.
FIG. 5B shows a detail view of the L-bracket heating element retainer shown in FIG. 5A.
FIG. 7 shows a side section view taken along line 7-7 of FIG. 6B.
FIG. 7A is a detail cross section view of the front stop shown in FIG. 7.
FIG. 7B shows a detail perspective view of the latch mechanism shown in FIG. 6B.
FIG. 13 shows a perspective view of a batch of aligners after they have been removed from the vacuum plate and cups.
FIG. 14 shows a perspective view of a single aligner on a disk that has been separated from the batch of aligners shown in FIG. 13.

DETAILED DESCRIPTION

Figure 1:
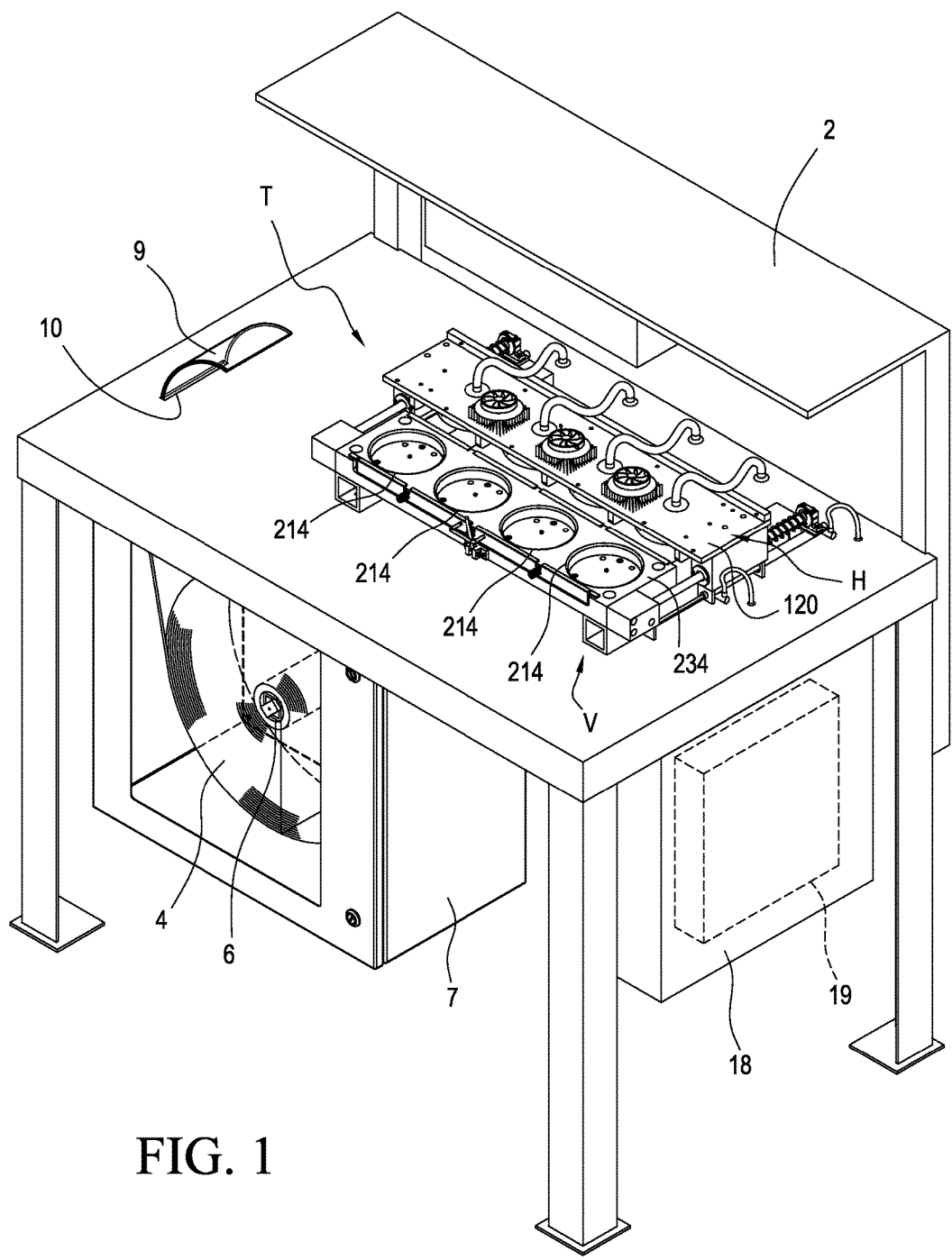
FIG. 1 shows a perspective view of an embodiment of the inventive thermoformer.

FIG. 1 shows the thermoformer T as typically used together with a table 2. The thermoformer T includes generally the heater cap H and the vacuum plate V. A polymer enclosure 7 includes a polymer roll 4. The polymer roll 4 is mounted on a spool 6, which allows the polymer 9 to be fed freely from the spool 6. The polymer 9 is fed through slot 10 to the upper surface 234 of the vacuum plate V. The polymer 9 used with the invention is a polymer such as polyurethane. For example, the proprietary formulation sold under the trademark Zendura® may be used. It is contemplated that alternative polymer formulations or acrylic or other materials may also be used. Polymer sheets 12 (see FIG. 6A) are formed from the spool 6 of polymer 9, but individual polymer sheets 12 may be provided independently from the spool 6. Also shown in FIG. 1 is the enclosure 18, which encloses the controller 19. The controller includes the electronics and other controls required for the thermoformer T.

Figure 2:
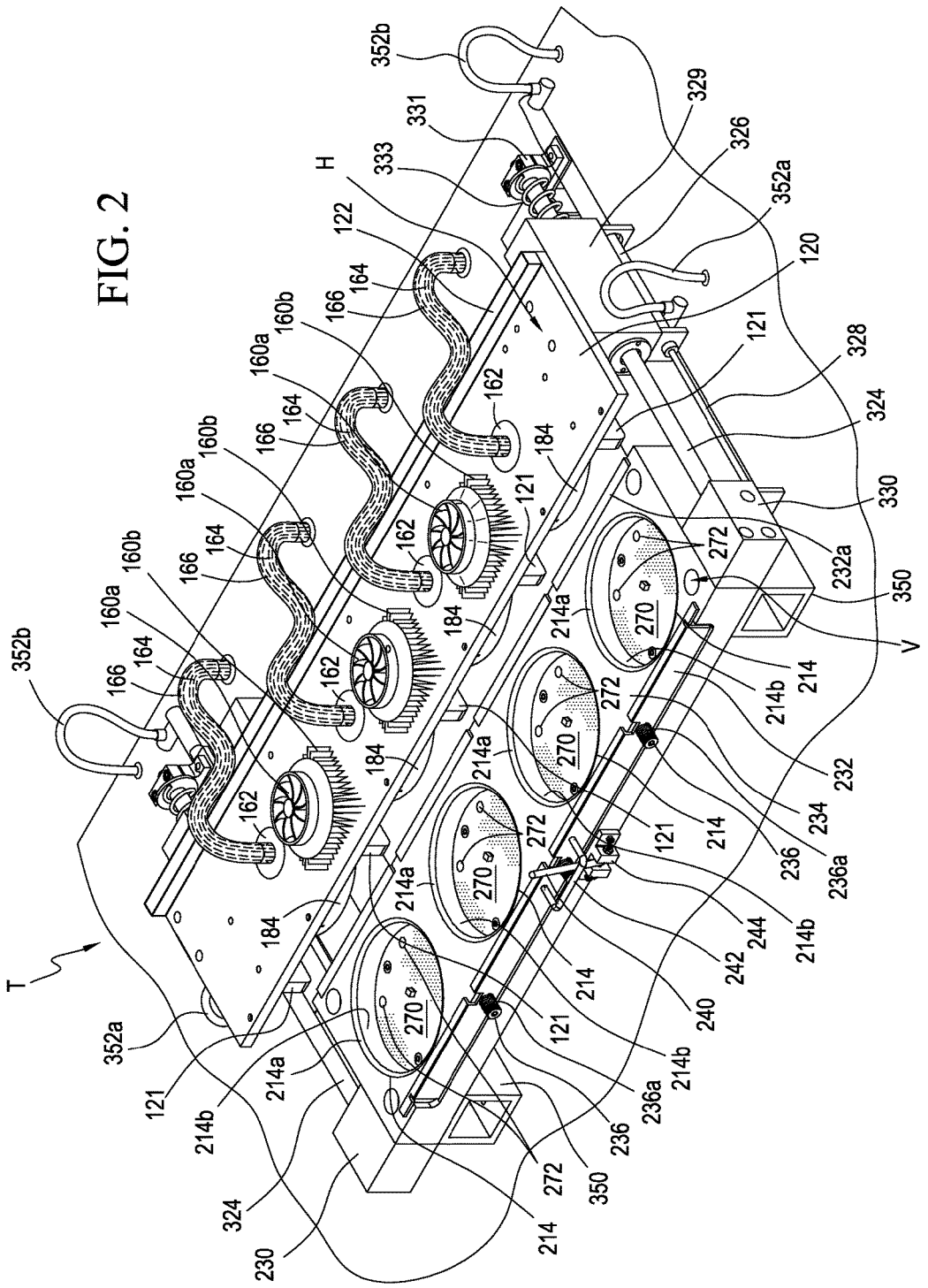
FIG. 2 shows a detailed perspective view of an embodiment of the inventive thermoformer.

Refer now to FIG. 2 where the thermoformer T is shown. The vacuum plate V has a plurality of cups 214 extending below the surface 234. Each cup 214 has a rounded edge 214a at the intersection of the wall 214b of the cup 214 with the upper surface 234 of the vacuum plate V. Although four (4) cups 214 are shown in FIG. 2 and throughout the figures provided herein, more than four (4) cups 214 can be provided to increase production as desired.

The heater cap H includes the heater cap plate 120 and the back plate 122, which is attached to the heater cap plate 120. A plurality of heating elements 162 are mounted below the heater cap plate 120, as will be described in detail later. The heater cap plate 120 is attached to the housing block 329. The housing block 329 is free to move forward and back along shaft 324 to position the heater cap plate 120 above the vacuum plate V surface 234 so that the plurality of heating elements 162 are positioned in proximity to the plurality of cups 214 in the vacuum plate V.

Figure 3B:
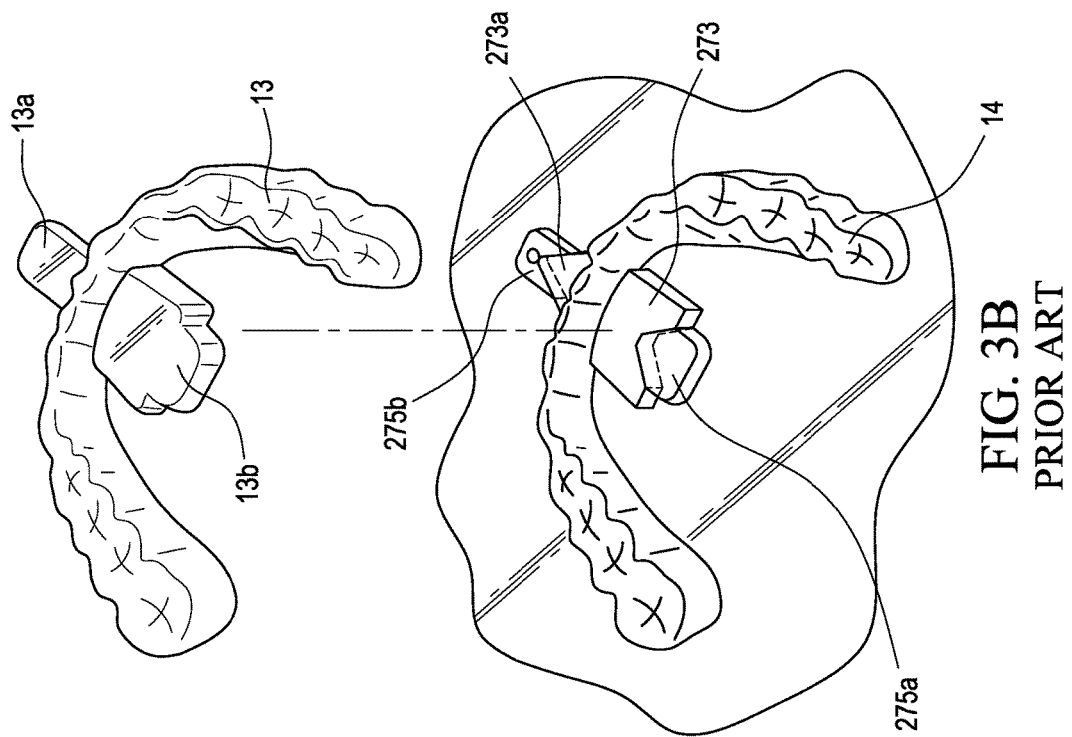
FIG. 3B shows a perspective view of an embodiment of a prior art dental model and a prior art aligner.
Figure 3A:
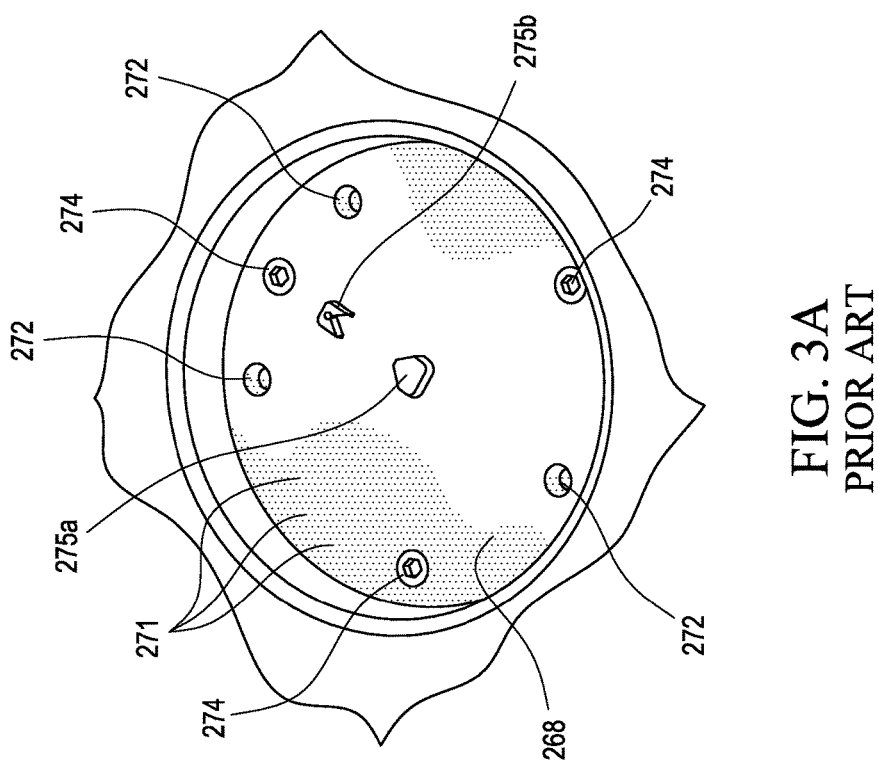
FIG. 3A shows a perspective view of a prior art adapter plate inside of a cup.
Figure 3D:
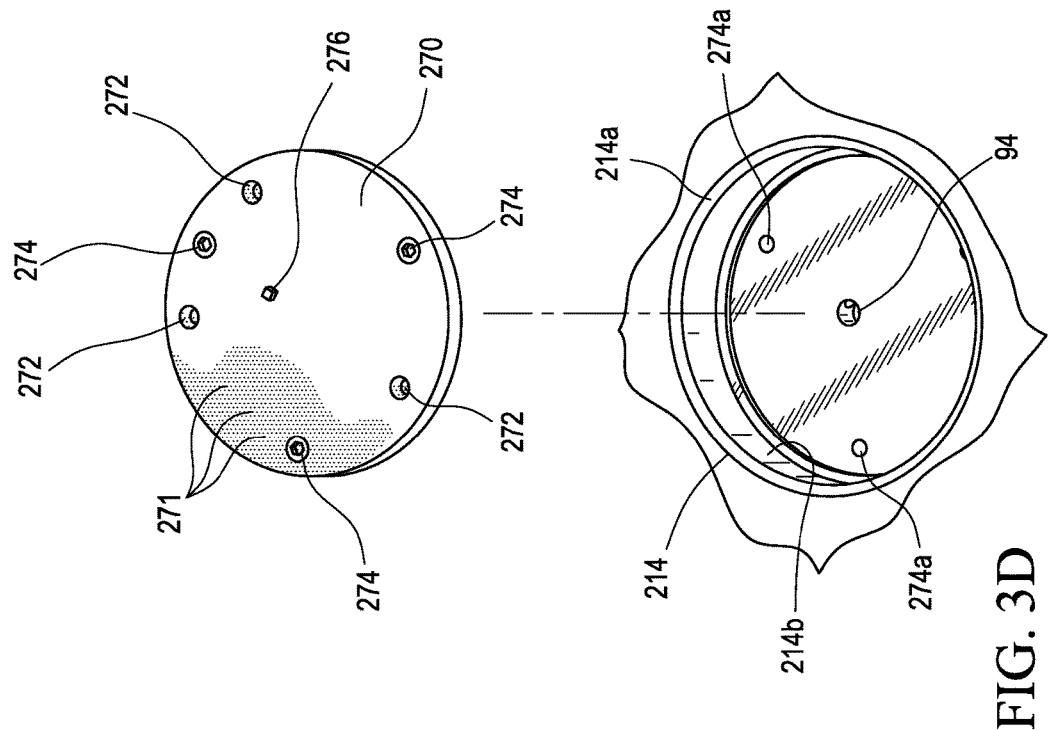
FIG. 3D shows a perspective assembly view of an embodiment of an inventive adapter plate and a cup.
Figure 3C:
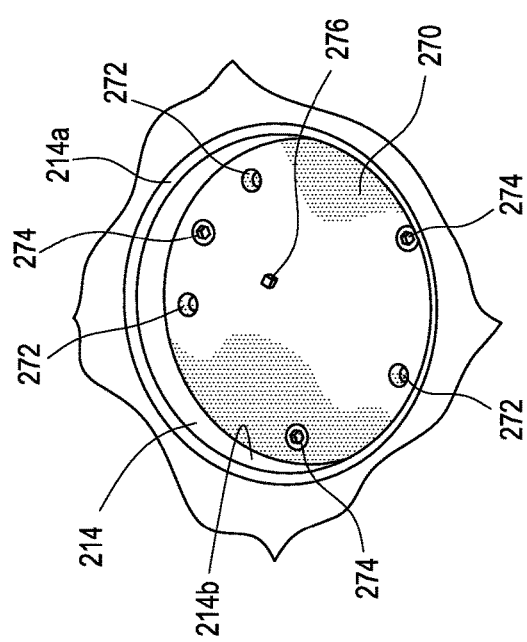
FIG. 3C shows a perspective view an embodiment of an inventive adapter plate inside of a cup.

FIG. 3A shows a prior art adapter plate. FIG. 3B shows a prior art dental model 14 and prior art aligner 13. FIG. 3C shows adapter plate 270 of the present invention and FIG. 3D shows an inventive adapter plate 270 and a cup 214 of the present invention. Both the prior art adapter plate 268 and the inventive adapter plate 268 include a plurality of indentations 272 and a plurality of mounting screws 274. Mounting screws 274 are used to attach each adapter plate 270 to the bottom of the cups 214. The mounting screws 274 attached to the mounting screw holes 274a (see FIG. 3D).

Refer now to FIGS. 3A and 3B. The prior art adapter plate 268 includes both a spear shaped post 275a and a spear locator 275b. The spear shaped post 275a engages tab 273 on the prior art dental model 14. Tab 273 is located on the lingual side of the anterior teeth, tongue side of the front teeth. The spear locator 275b is positioned on the lip side of the front teeth. The spear locator 275b engages with the prior art spear 273a of the prior art dental model 14. The inventors have discovered that the presence of the spear 273a on the prior art dental model 14 creates a reduced area between the top of the spear 273a and the gum line, as well as creating a vertical webbing. The vertical webbing, sometimes called a crease or pinch of polymer, must be trimmed away by hand. Sometimes trimming the unwanted vertical webbing from the prior art aligner 13 results in too little gum coverage, which results in a defective, rejected aligner.

The inventive adapter plate 270 shown in FIGS. 3C and 3D includes a peg 276 onto which the socket 276a of the dental model 15 is positioned (also see FIG. 4A). The peg 276 extends through the tab 276a. The use of the peg 276 instead of the spear shaped post 275a and the spear locator 275b simplifies and improves the thermoforming of each aligner 16 by eliminating the undesirable vertical webbing and by reducing the number of components required on the adapter plate 270. The peg 276 is typically formed by pressing an aluminum plug into the sintered adapter plate 270, then machining the peg 276 to the desired square or rectangular shape. Other techniques may also be desired to form the peg 276 as desired.

FIG. 3D shows how the adapter plate 270 fits into cup 214. Also shown in FIG. 3D is the vacuum port 94 at the base of the cup 214.

In FIG. 4B an adapter plate 270 is shown positioned in each of the plurality of cups 214. Each adapter plate 270 is typically constructed of a sintered metal such as sintered bronze, but other porous materials may also be used.

Also shown in FIG. 4B are three (3) dental models 15 positioned in cups 214 on adapter plates 270. A single dental model 15 is shown with a positioning line 15a. The positioning line 15a illustrates how the dental model 15 is positioned onto the adapter plate 270.

FIG. 5A is a side sectional view taken along line 5-5 of FIG. 4B. In FIG. 5A, a dental model 15 is shown in cup 214. Also shown in FIG. 5A is an outer side of a heating element 162 and an outer lip 162a of the heating element 162. Each heating element 162 is secured to the underside of the heater cap plate 120 with an L-bracket 188 that extends under the underside of the outer lip 162a of the heating element 162. FIG. 5B shows a detail view of the heating element 162 L-bracket 188. The L-bracket 188 is secured to the inside of the circular wall 184, which surrounds each outer lip 162a. The L-bracket 188 includes a slot 186 in the tab 188a through which a lock screw 186a is positioned. The lock screw 186a attaches to the circular wall 184. The L-bracket 188 also allows the heating element 162 to be removed or replaced from below the heater cap plate 120 as required.

It is contemplated that alternative heating elements may be used instead of the heating element 162 described and shown. For example, alternative ceramic or composite or bulb type heating elements may be used in square, round, oval or other desired shapes.

Figures 6A, 6B:
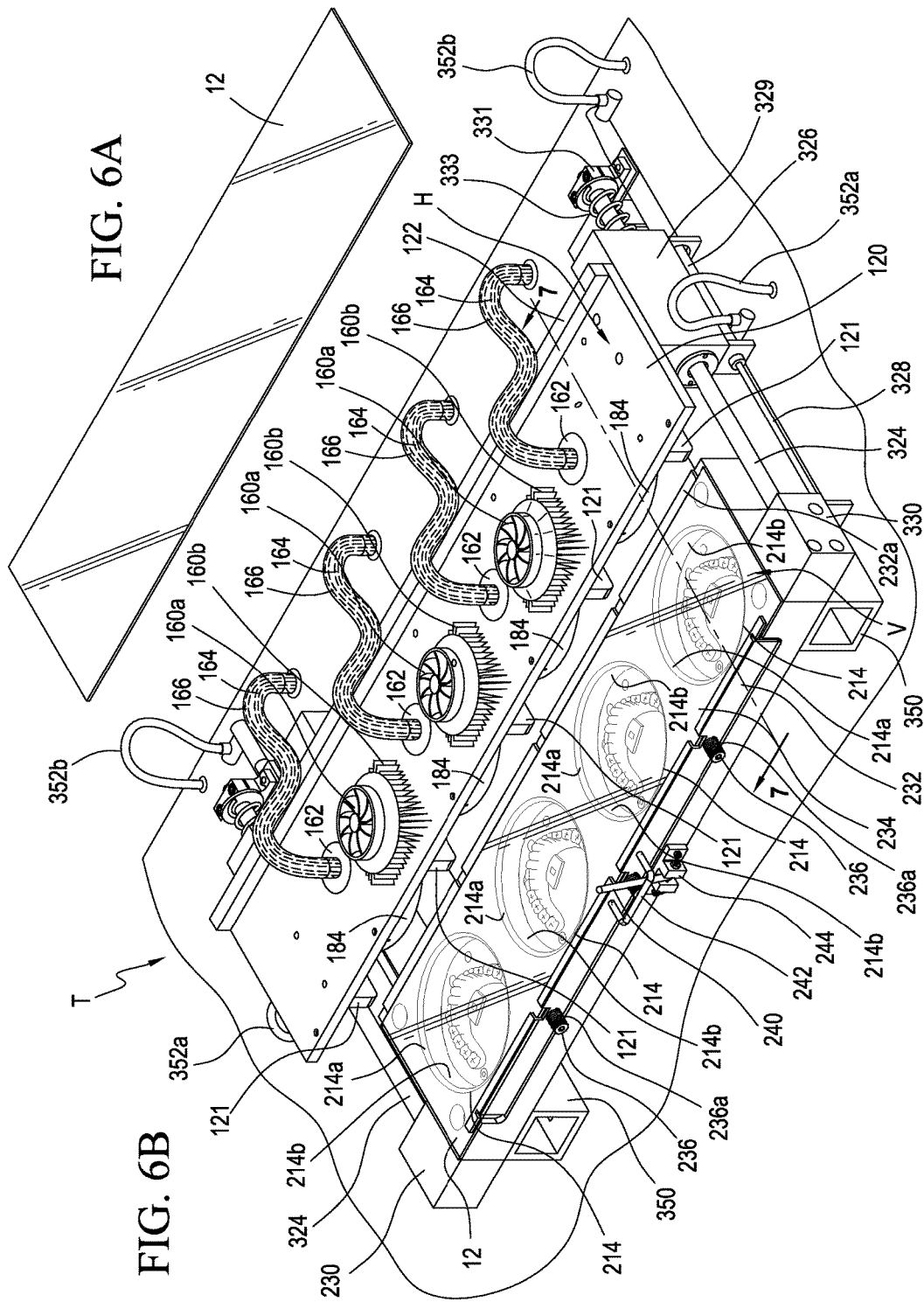
FIG. 6A shows a perspective view of a polymer sheet.
FIG. 6B shows a perspective view of an embodiment of the inventive thermoformer with a polymer sheet covering the surface of the vacuum plate and the cups.

In FIG. 6A a polymer sheet 12 is shown. The polymer sheet 12 is comprised of polymer material 9 (see FIG. 1) that has been cut to a size that corresponds to the upper surface 234 of the vacuum plate V. In FIG. 6B the polymer sheet 12 is shown positioned on the upper surface 234 of the vacuum plate V. A side sectional view taken along line 7-7 of FIG. 6B is shown in FIG. 7. The polymer sheet 12 is positioned on the upper surface 234 of the vacuum plate V between the front stop 232 and rear stop 232a. FIG. 7A shows a detail of the front stop 232 in relation to the polymer sheet 12. A compression screw 236 compresses a compression spring 236a to provide the desired tension against the front edge of the polymer sheet 12. As best seen in FIG. 6B and the detail view in 7B, the front stop 232 can be pulled away from the front edge of the polymer sheet 12 by pulling the lever 240, which rotates about the pivot block 244, towards the handle 242 thereby urging the front stop 232 away from the front edge of the polymer sheet 12. The back edge of the polymer sheet 12 is constrained by the rear stop 232a. The overall compression imposed on the polymer sheet between the front stop 232 and the rear stop 232a is controlled by the adjustable compression screw 236 and compression spring 236a. The rear stop 232a is shown as a groove machined into the upper surface 234 of the vacuum plate V, but a separate member attached to the upper surface 234 may also be used to restrain the back edge of the polymer sheet 12.

Figure 8:
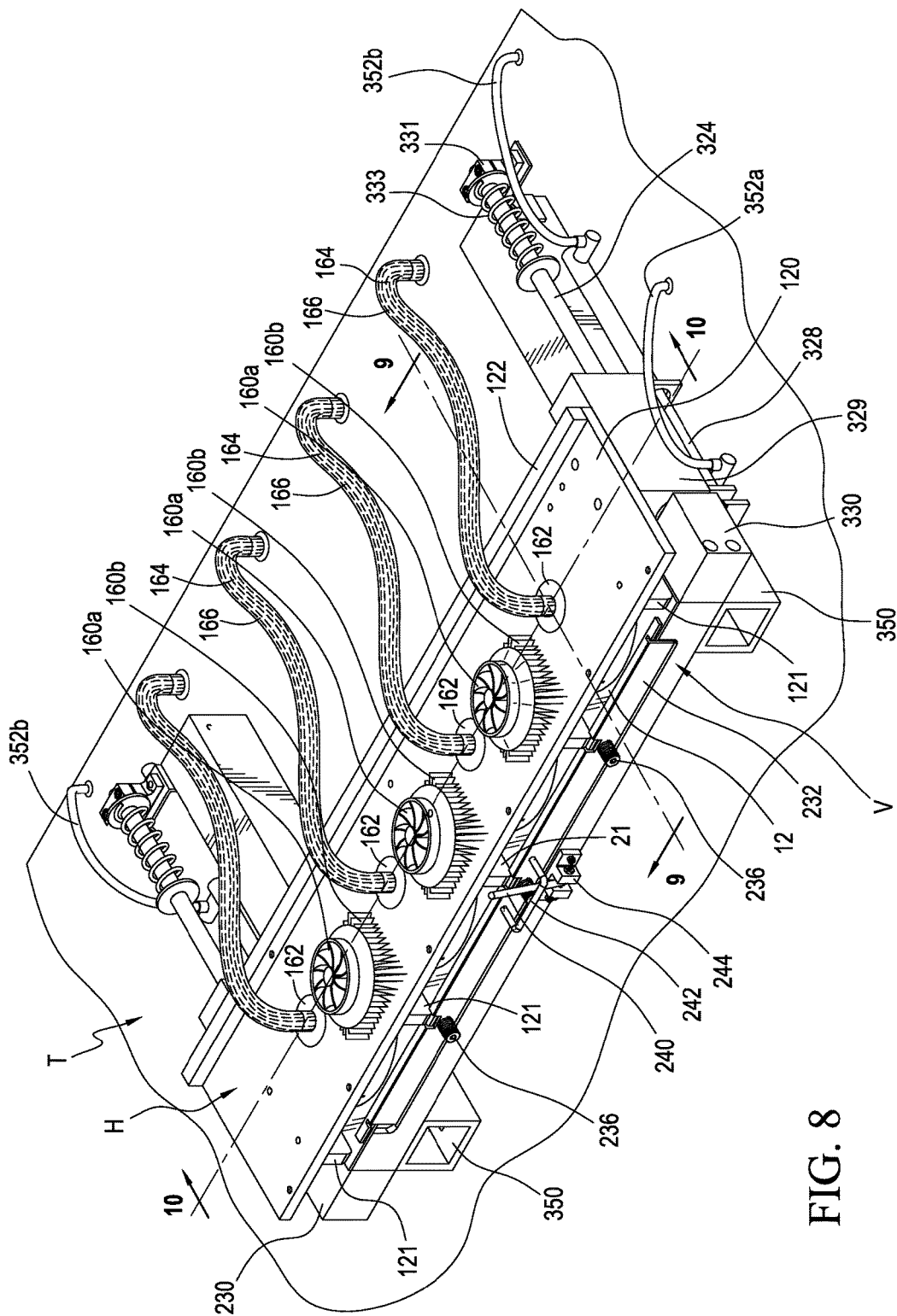
FIG. 8 shows a perspective view of an embodiment of the inventive thermoformer with the heater cap positioned over the vacuum plate.
Figure 9:
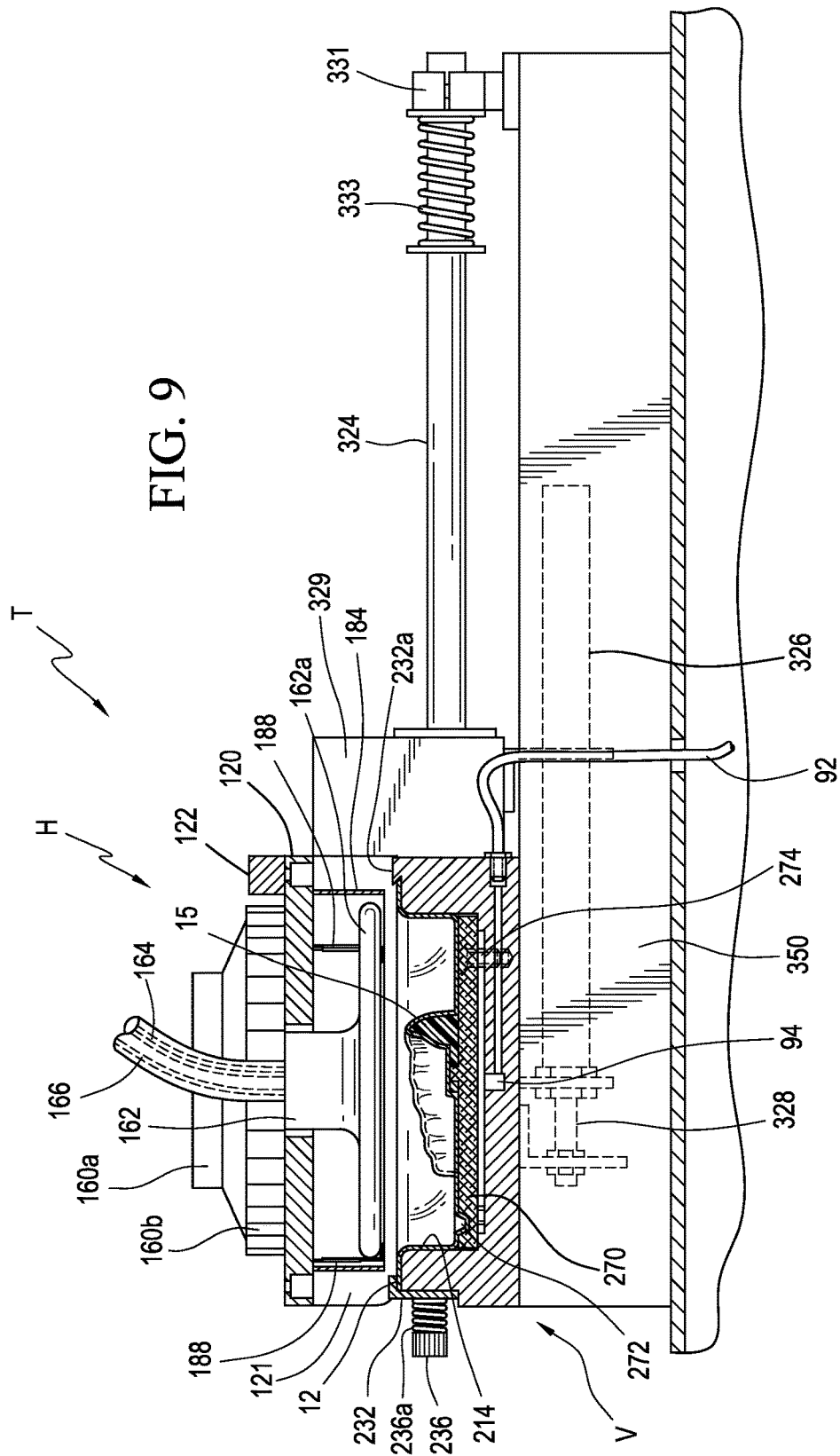
FIG. 9 shows a side section view taken along line 9-9 of FIG. 8.

In FIG. 8 the heater cap H is shown covering the vacuum plate V. A cross side section view taken along line 9-9 of FIG. 8 is shown in FIG. 9. After the dental models 15 are in position in the cups 214 and a polymer sheet 12 is on the vacuum plate upper surface 234, the heater cap H is moved above the vacuum plate V. When the heater cap H is above the vacuum plate V, the heating elements 162 will be in proximity to the cups 214, which contain the dental models 15.

The position of the housing block 329 and heating cap H are controlled by pneumatic pressure. When pneumatic pressure is applied to the closing pressure line 352a air cylinder 328 is actuated. When air cylinder 328 is retracted the entire heating cap H moves forward. The housing block 329 moves forward on shaft 324. As the housing block 329 moves forward, the heater cap plate 120 also moves forward to position the heater cap plate 120 and heating elements 162 above the vacuum plate V.

After the heater cap H is above vacuum plate V, heat is applied to the polymer sheet 12 with heating elements 162. Power is applied to heating elements 162 with power conductors 164 (shown in hidden lines connected to heating elements 162). The temperature of each heating element 162 can be individually controlled based on information received from the thermocouple 166, (also shown connected to heating elements 162 with hidden lines). Cooling fans 160a with cooling fins 160b are shown positioned on the top of the heater cap plate 120. The cooling fans 160a can control the temperature of the heater cap plate 120 during repeated production cycles to manage the temperature of the heater cap plate 120. The position of the heater cap H can also be controlled hydraulically instead of pneumatically, as desired.

A vacuum port 94 is shown that opens into the bottom of the cup 214 (best seen in FIGS. 3D and 9). The vacuum port 94 is connected to vacuum source 92. After the heating elements 162 are activated to cause the polymer sheet 12 to reach the desired temperature set point, a vacuum is drawn by vacuum source 92 to evacuate the cups 214. The adapter plate 270 includes a plurality of orifices 271 (see FIG. 3D) so a vacuum drawn through the vacuum port 94 from a vacuum source 92 draws a vacuum efficiently inside the cup 214.

Figure 10:
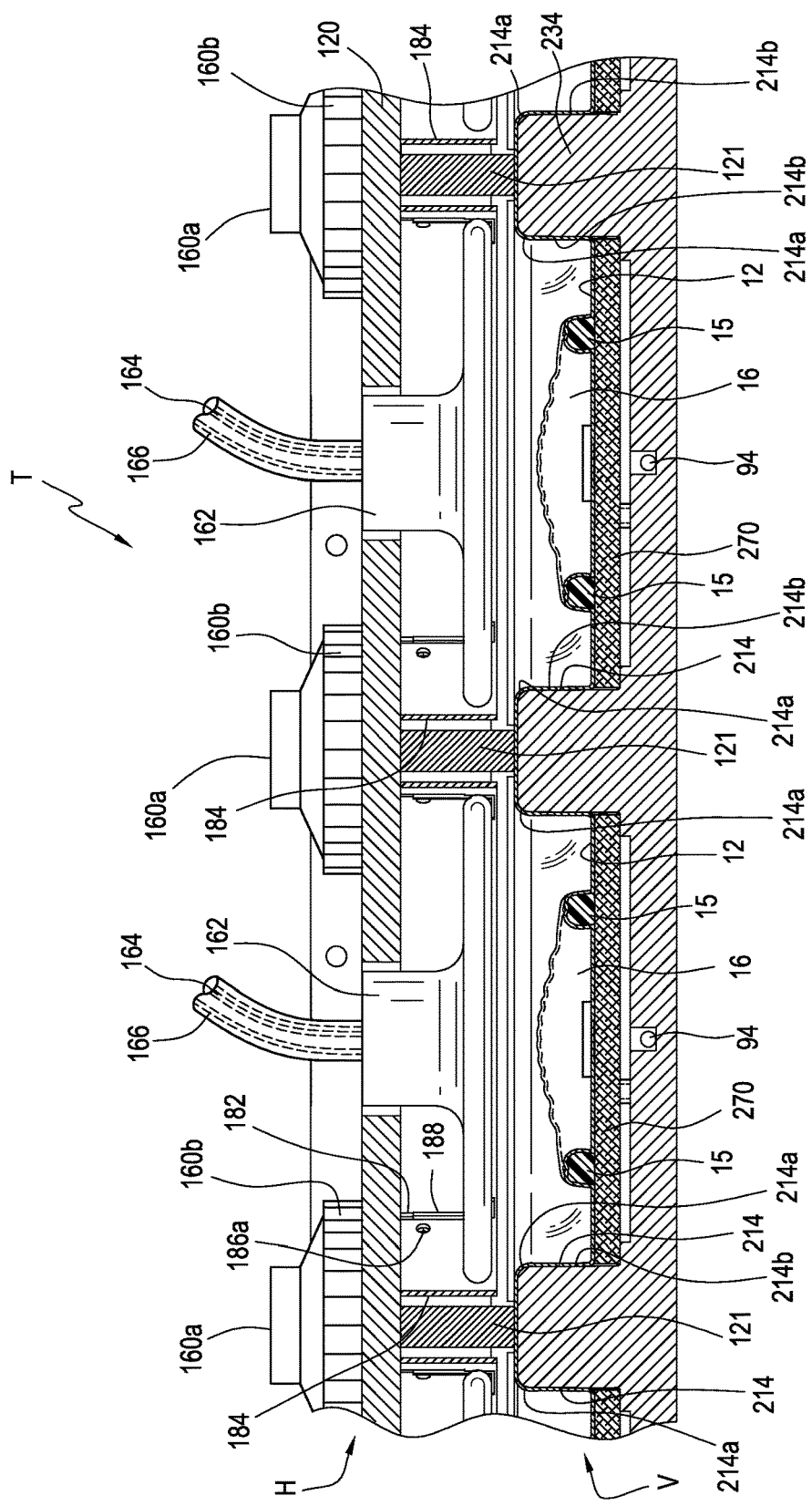
FIG. 10 shows a front section view taken along line 10-10 of FIG. 8.

FIG. 10 is a front cross section view taken along line 10-10 of FIG. 8. Boss 121 is attached to the underside of the heater cap plate 120. When the heater cap H is moved forward to cover the vacuum plate V, each boss 121 secures the polymer sheet 12 between each cup 214 to prevent air from escaping from between the polymer sheet 12 and the cup 214. The polymer sheet 12 above each cup 214 can then be drawn into each cup 214 as a vacuum is drawn from vacuum port 94.

An effective seal is formed between the polymer sheet 12 and the rounded edge 214a that is formed between the cup wall 214b and the upper surface 234 of the vacuum plate V so that when a vacuum is drawn through vacuum port 94 the polymer sheet 12 that is above each cup 214 is pulled downwardly into the cup to form onto each dental model 15.

Figure 11:
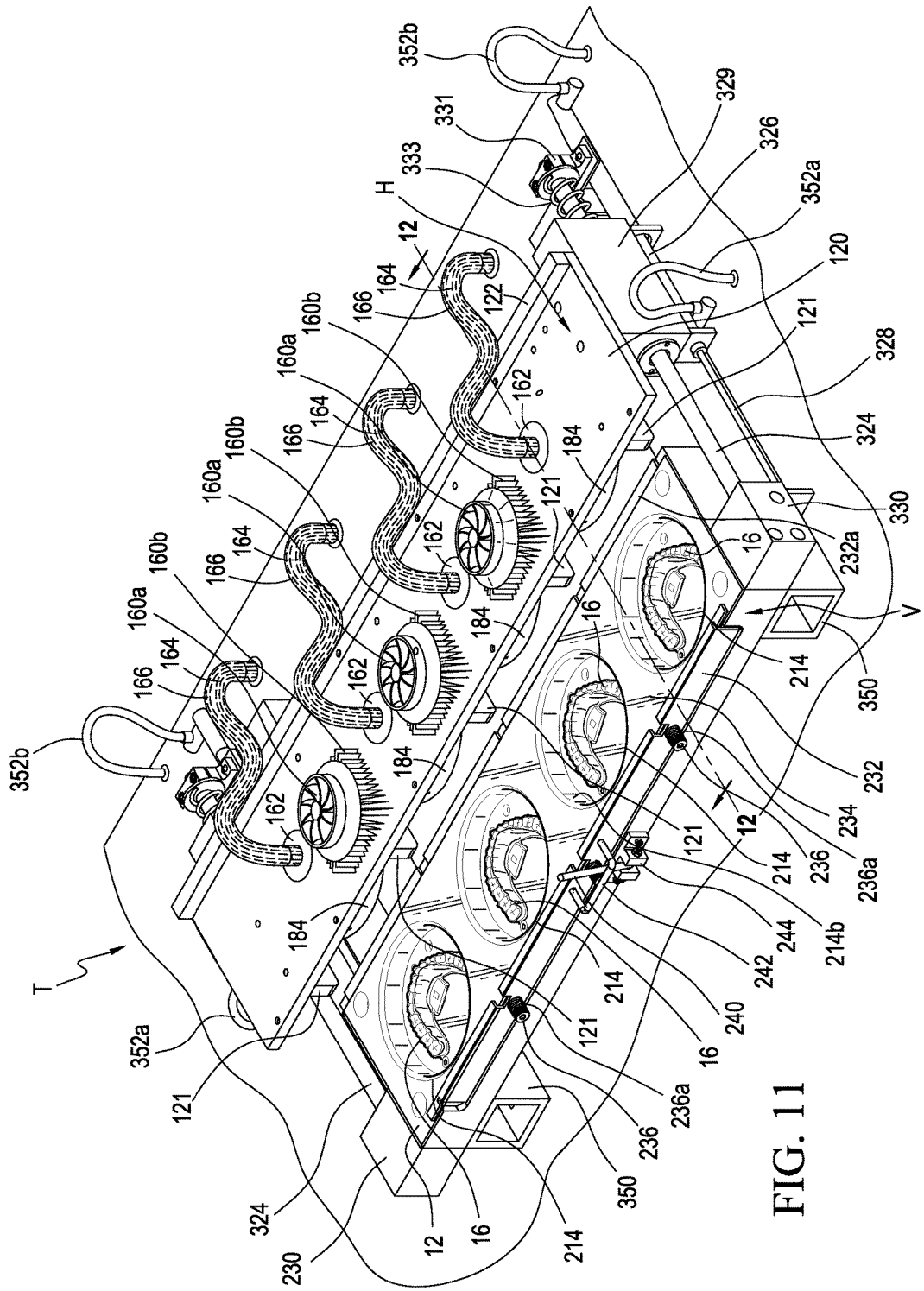
FIG. 11 shows a perspective view of an embodiment of the inventive thermoformer with a polymer sheet molded over dental models.
Figure 12:
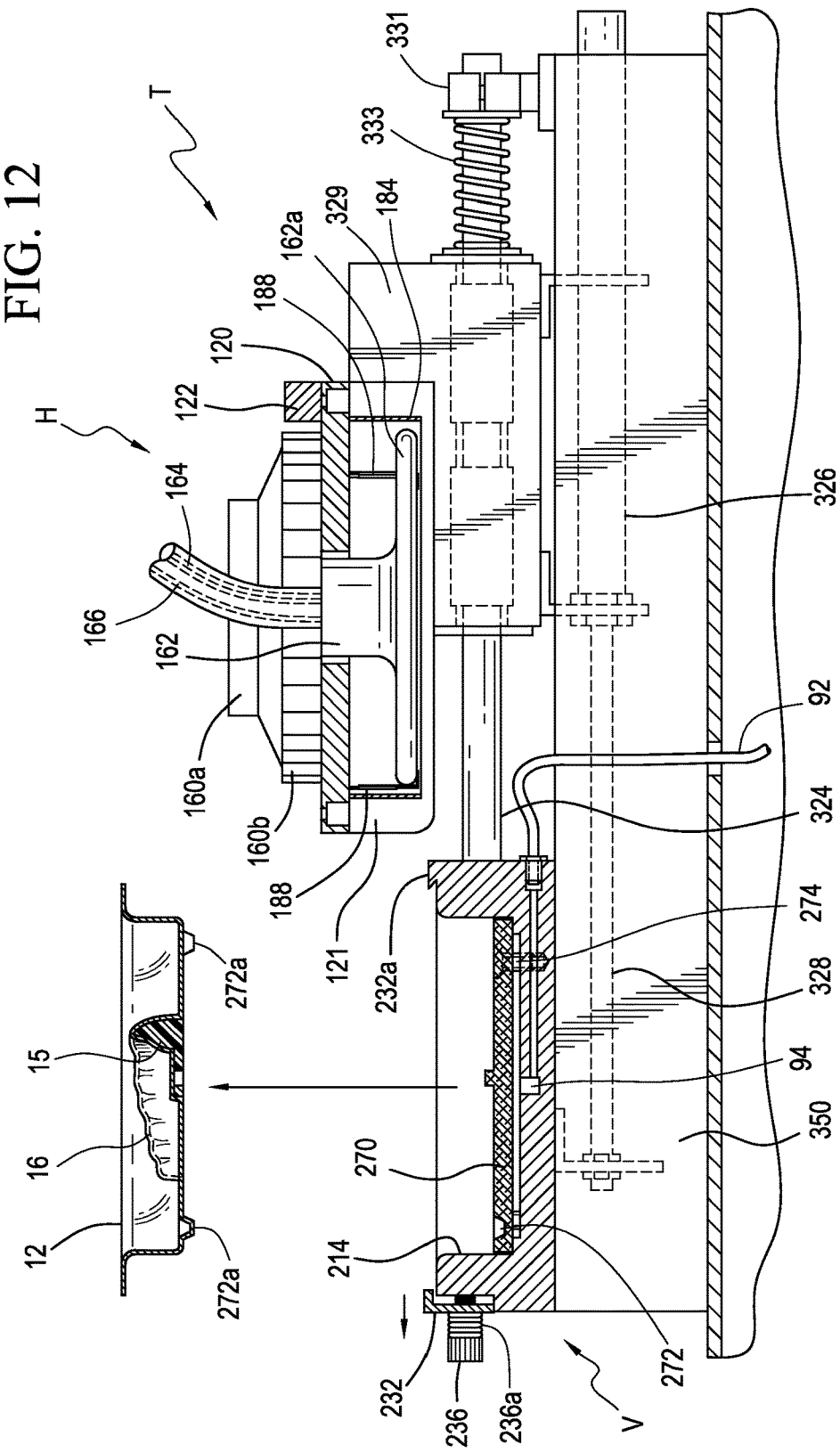
FIG. 12 shows a side section view taken along line 12-12 of FIG. 11.

After heat has been applied to the polymer sheet 12 and a vacuum has been drawn in the cups 214, the polymer sheet 12 molds about the surface of each dental model 15 as seen in FIGS. 11 and 12. After the polymer sheet 12 has been molded about the surface of each dental model 15, the heater cap H is moved rearward to expose the molded aligners 16 (see FIGS. 11 and 12). Pneumatic pressure is applied to opening line 352b to extend cylinder 328 to force heater block 329 and the attached heater cap H to move rearward, away from the vacuum plate V. A spring 333 is provided on shaft 324 to dampen the motion of the heater cap H as it opens by resisting the rearward motion of the housing block 329.

Often the dental models come out of the cups 214 together with the aligners 16 and they are then removed therefrom. Each aligner includes formed indentations 272a that are formed from the indentations 272 in the adapter plates 270. The formed indentations may be used for subsequent handling of the aligner 16 before it has been trimmed and buffed.

FIG. 13 shows a batch of molded aligners 16 that have been removed from the heater cap H. The batch of aligners 16 are separated into individual aligners by punching a disk 17 from the polymer segment 12 with a die cutter or other tool as indicated at lines 12a, 12b, 12c and 12d. The resulting aligner 16 on disk 17 shown in FIG. 14 is then ready for further processing to cut, finish and uniquely identify each aligner 16.

Figure 15:
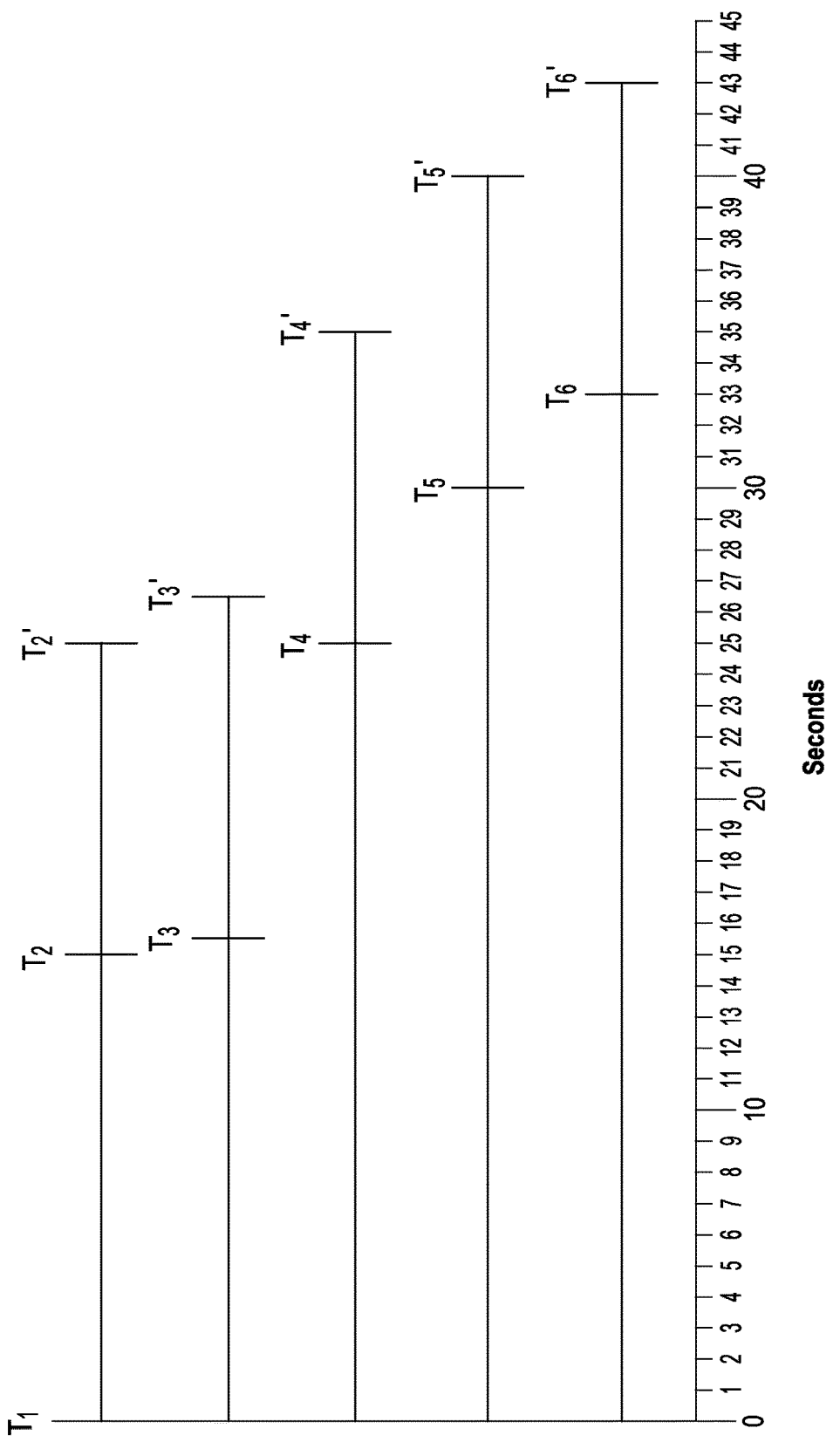
FIG. 15 shows a timeline of an embodiment of the inventive thermoforming process showing vacuum phases.

Process Steps:

An embodiment of the process steps, including vacuum phases, of manufacturing aligners with the inventive thermoformer as illustrated based on the timeline in FIG. 15 is as follows:

1) At T1 the operator engages two momentary switches (not shown) simultaneously, which causes the heater cap H to close. Each momentary switch requires engagement by each of the operator's hands to prevent the operator from getting either hand in the moving parts of the thermoformer T.

2) The polymer sheet 12 undergoes heating above each cup 214 for a predetermined period of time between T1 and T5/T5'. A typical time frame from when the buttons are pressed to when the heater cap H retracts is approximately 25-35 seconds (T1 to T5/T5').

3) The polymer sheet 12 above each cup 214 is subjected to a "pre-stretch" at a predetermined time T2. The predetermined "pre-stretch" time typically begins about 15-25 (T2-T2') seconds after the switches are engaged at T1 and lasts for a predetermined period of time, which is typically about 0.5-1.5 seconds (between T3 to T3'). The "pre-stretch" is produced by opening the vacuum source 92 and achieving an absolute pressure of 13+/−1 in. Hg. The timing of the "pre-stretch" vacuum is established electronically independent of the operator's commands. The "pre-stretch" is performed to make more polymer 9 available around the adapter plate 270 for the final stretch. If there is too long of a "pre-stretch" undesirable wrinkles may develop in the portion of the polymer sheet 12 in each cup from which air was not able to escape. Too short of a "pre-stretch" and there may not be enough polymer 9 from the polymer sheet 12 introduced and thus the aligner 16 could be too thin. It was determined by the inventors that by adding the "pre-stretch" sequence to the thermoforming process, the thinning problem was solved.

4) The final pull, in which a vacuum is drawn by the vacuum source 92 to approximately 28+/−1 in. Hg vacuum, is activated at T4/T4' approximately 25-35 seconds after the initial process has started at T1. The heater cap H is pulled back at T5/T5', approximately 30-40 seconds after the initial process started at T1.

5) The final pull continues between T4/T4' and T6/T6' for about 3-12 seconds at which time the aligners 16 are completed and ready to be removed from the vacuum plate V.

The process steps can vary from the time periods specified without varying from the inventive thermoforming process. Also, instead of measuring the time between the process steps shown in FIG. 15, a delta or change in pressure between steps at T1-T6 can be used to determine when the process steps are performed.

The timing and duration of the "pre-stretch" and the final pull and the amount of vacuum provided are approximate ranges and the ranges can vary from the amounts stated without departing from the scope of the inventive system and method.

Thus specific embodiments and methods of a batch thermoformer for dental appliances have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. System for thermoforming a batch of dental appliances simultaneously comprising:
   a. A vacuum plate having an upper surface and a plurality of cups for receiving individually unique dental models, each of said cups being formed from a wall together with an integral base;
   b. A polymer sheet extending over said upper surface of said vacuum plate and over said cups;
   c. A heater cap being movable in proximity to said cups to heat the polymer sheet to be formed onto the dental models;
   d. Said vacuum plate configured to create a vacuum seal between an upper edge that is formed between the wall of each of said cups and said upper surface of said vacuum plate and the polymer sheet; and
   e. A vacuum source to create a vacuum in said cups below the polymer sheet wherein the pressure contained in said cups is lower than atmospheric pressure whereby at least a portion of polymer from the polymer sheet is drawn downwardly across each said upper edge of said cups and into each of said cups and said polymer is drawn over the dental models to form an aligner over each of the dental models.

2. System for thermoforming a batch of dental appliances simultaneously according to claim 1 wherein the vacuum seal between said upper edge of said cups and the polymer sheet is rounded to create an effective seal between the polymer sheet and said upper surface of said vacuum plate.

3. System for thermoforming a batch of dental appliances simultaneously according to claim 1 wherein said heater cap includes a plurality of heating elements with each heating element aligned to provide heat in proximity to each of said cups.

4. System for thermoforming a batch of dental appliances simultaneously according to claim 3 wherein each of said heating elements includes a thermocouple in communication with a controller to individually monitor and adjust the temperature of said heating elements whereby the temperature of each of said cups can be controlled independently.

5. System for thermoforming a batch of dental appliances simultaneously according to claim 3 wherein a plurality of cooling fans is provided on said heater cap to regulate the temperature of said heater cap.

6. System for thermoforming a batch of dental appliances simultaneously according to claim 1 wherein an adapter plate having a plurality of orifices is positioned in each of said cups whereby vacuum is applied by said vacuum source through the orifices in said adapter plate to effect uniform molding of the polymer sheet about the dental model to form the aligner.

7. System for thermoforming a batch of dental appliances simultaneously according to claim 6 wherein said adapter plate comprises a sintered metallic material.

8. System for thermoforming a batch of dental appliances simultaneously according to claim 6 wherein said adapter plate includes an alignment feature to orient the dental model in a desired location to enable later processing of the aligner.

9. System for thermoforming a batch of dental appliances simultaneously according to claim 8 wherein said alignment feature comprises a peg, integral with said adapter plate, onto which the dental model is secured.

10. System for thermoforming a batch of dental appliances simultaneously according to claim 1 wherein said heater cap includes a plurality of bosses adapted to present the polymer sheet to the upper surface of the vacuum plate to prevent air from escaping from between the polymer sheet and the cup when the heater cap is in proximity to the vacuum plate and when the vacuum source draws a vacuum in the cup.

11. System for thermoforming a batch of dental appliances simultaneously according to claim 1 wherein at least one cylinder is provided to extend and retract said heater cap to position said heater cap in proximity to said vacuum plate.

12. System for thermoforming a batch of dental appliances simultaneously according to claim 11 wherein a spring is positioned behind said at least one cylinder to dampen said heater cap when said heater cap is opened.

13. System for thermoforming a batch of dental appliances simultaneously according to claim 11 wherein pneumatic pressure is applied to the at least one cylinder to extend and retract said heater cap.

14. System for thermoforming a batch of dental appliances simultaneously according to claim 1 wherein a stop is provided on the upper surface of the vacuum plate positioned at the rear of said plurality of cups to engage a back edge of the polymer sheet and an adjustable stop is provided on the upper surface of the vacuum plate positioned to engage a front edge of the polymer edge of the polymer sheet, wherein the front edge is substantially parallel to the back edge of the polymer sheet whereby the polymer sheet can be positioned as desired relative to said cups.

15. System for thermoforming a batch of dental appliances simultaneously according to claim 1 wherein the vacuum is drawn to approximately 1.0 psia.

16. System for thermoforming a batch of dental appliances simultaneously according to claim 9 wherein said peg is positioned on said adapter plate and said dental model has a socket that is positioned on said peg whereby said peg is positioned below said dental model so that the polymer sheet is not torn by said peg during the molding of said aligner.

* * * * *